(12) United States Patent
Stevens et al.

(10) Patent No.: US 8,318,206 B2
(45) Date of Patent: Nov. 27, 2012

(54) PARTICLES

(75) Inventors: Molly M. Stevens, London (GB); Rein Ulijn, Glasgow (GB); Anna Sague Laromaine, Cassà de la Selva (ES); Liling Koh, Singapore (SG)

(73) Assignee: Imperial Innovations Limited, London (GB)

( * ) Notice: Subject to any disclaimer, the term of this patent is extended or adjusted under 35 U.S.C. 154(b) by 777 days.

(21) Appl. No.: 12/095,408

(22) PCT Filed: Nov. 29, 2006

(86) PCT No.: PCT/GB2006/004459
§ 371 (c)(1),
(2), (4) Date: Mar. 20, 2009

(87) PCT Pub. No.: WO2007/063300
PCT Pub. Date: Jun. 7, 2007

(65) Prior Publication Data
US 2009/0181097 A1     Jul. 16, 2009

(30) Foreign Application Priority Data
Nov. 29, 2005    (GB) .................................. 0524313.4

(51) Int. Cl.
*A61K 9/14* (2006.01)
*C12Q 1/37* (2006.01)
(52) U.S. Cl. ........................................ 424/489; 435/23
(58) Field of Classification Search .................. 424/489; 435/23
See application file for complete search history.

(56) References Cited

U.S. PATENT DOCUMENTS
2009/0004118 A1*  1/2009  Nie et al. ..................... 424/9.35

FOREIGN PATENT DOCUMENTS
WO    WO-02/098364    12/2002
WO    WO-2005/100602  10/2005

OTHER PUBLICATIONS

Bosma et al., Chem. Commun. 2003, pp. 2790-2791.
Castner et al., Surface Science 500, 2002, pp. 28-60.
Chang et al., Biochem. and Biophysical Research Commun., 2002, vol. 334, No. 4, pp. 1317-1321.
Coombs et al., Chemistry & Biology, 1998, vol. 5, No. 9, pp. 475-488.
Davis et al., PNAS, 2002, vol. 99, No. 4, pp. 2222-2227.
Doeze et al., Angew. Chem. Int. Ed. 2004, vol. 43, pp. 3138-3141.
Greener et al., Journal of Wound Care, 2005, vol. 14, No. 2, pp. 59-61.
Humphrey et al., J. Am. Chem. Soc., 2003, vol. 125, No. 46, pp. 13952-13953.
International Preliminary Report on Patentability for PCT/GB2006/004459, Nov. 1995.
International Search Report for PCT/GB2006/004459, Aug. 2007.
Kanaras et al., Angew. Chem. Int. Ed. 2003. vol. 42, No. 2, pp. 191-194.
Katz et al., Angew. Chem. Int. Ed. 2004, vol. 43, pp. 6042-6108.
Maly et al., Chembiochem, 2002, vol. 3, pp. 16-37.
Mazhar et al., BJU International, 2006, vol. 98, pp. 725-730.
Mirkin et al., Nature, vol. 382, Aug. 15, 1996, pp. 607-609.
Mrksich, Curr. Opinion in Biochem., 2002, vol. 6, pp. 794-797.
Niemeyer, Angew. Chem. In. Ed. 2001, vol. 40, pp. 4128-4158.
Perez et al., Biochem., 2004, vol. 5, No. 3, p. 261-264.
Perez et al., Nature Biotechnology, 2002, vol. 2002, pp. 816-820.
Rawlings et al., Nucleic Acids Research, 2002, vol. 30, No. 1, pp. 343-346.
Rosi et al., Chem. Rev., 2005, vol. 105, pp. 1547-1562.
Shenhar et al., Acc. Chem. Res., 2003, Vo. 36, No. 7, pp. 549-561.
Stevens et al., Adv. Mater., 2004, vol. 16, No. 11, pp. 915-918.
Tirrell et al., Surface Science 500, 2002, pp. 61-83.
Uljin et al., Org. Biomol., 2003, vol. 1, pp. 1277-1281.
Uljin et al., J. Am. Chem. Soc., 2002, vol. 124, No. 37, pp. 10988-10989.
Uljin et al., J. Chem. Soc., Perkin Trans. 2, 2002, pp. 1024-1028.
Vertegel et al., Langmuir 2004, vol. 20, pp. 6800-6807.
Written Opinion for PCT/GB2006/004459, Nov. 2006.
Zhao et al., Angew. Chem. Int. Ed. 2003, vol. 42, No. 12, pp. 1375-1378.

* cited by examiner

*Primary Examiner* — Ganapathirama Raghu
(74) *Attorney, Agent, or Firm* — Choate Hall & Stewart LLP; Brenda Herschbach Jarrell; Jeffrey E. Buchholz

(57) ABSTRACT

The present invention provides a particle aggregate comprising particles linked to other particles via linkers that are capable of being cleaved by an enzyme. The particles may be linked directly to other particles by the linkers or may be linked indirectly by means of a binding moiety. The invention also provides a particle coupled to a binding moiety via a linker that can be cleaved by an enzyme. The present invention may be used in diagnosing a disease or condition associated with the enzyme, or may be used to treat such a disease or condition whereby the drug is retained in the particle aggregate until the linkers are cleaved by the enzyme.

10 Claims, 8 Drawing Sheets

Figure 2A – aggregated.

Figure 2B - dispersed
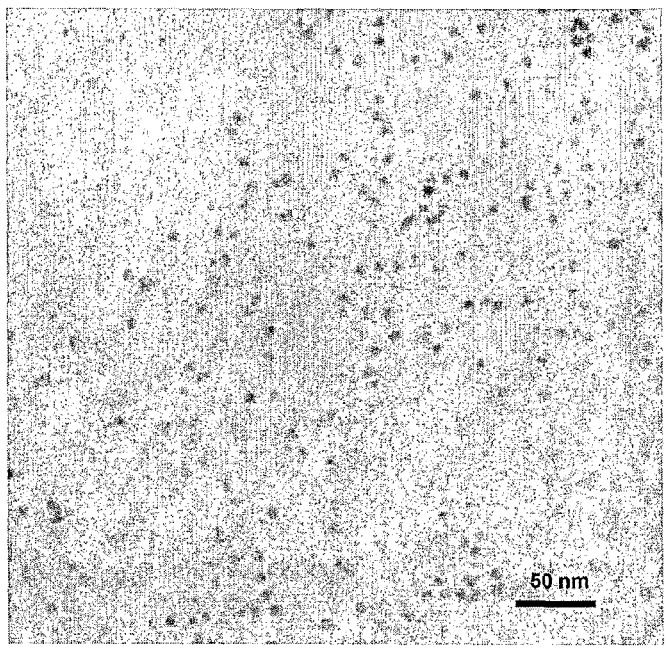
Figure 3
Approach 1
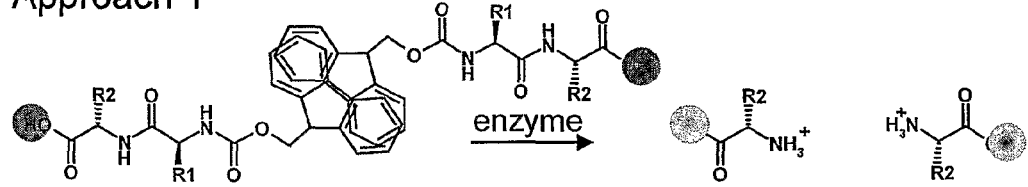
Approach 2
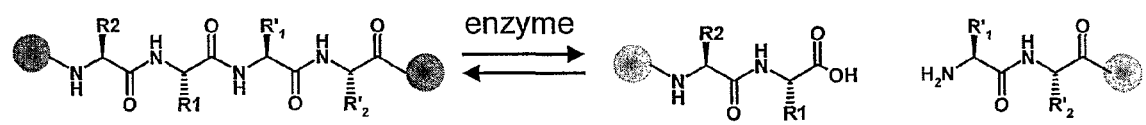

Figure 6A – Proteases involved in wound healing and their substrate specificity

| Proteases | | Enzyme Name(s) | | MW(kDa) | | Substrate | Substrate specificity | pI |
|---|---|---|---|---|---|---|---|---|
| | | MMP | Other names | latent | active | | | |
| MMP Families | Collagenases | MMP-1 | Collagenase -1, interstital collagenase | 52 | 43 | Collagens (I, II, III, VII, VIII, X, XI); gelatin; aggrecan; tenascin, L-selectin; IL-1β; proteoglycans; entactin; ovostatin; MMP-2; MMP-9 | Ac-Pro-Leu-Gly-Ser-Leu-Leu-Gly-OEt (SEQ ID NO: 6)<br>Mca-Pro-Leu-Gly~Leu-Dpa-Ala-Arg-NH$_2$ (SEQ ID NO: 7)<br>Pro-Met-Ala~Leu-Trp-Ala-Thr (SEQ ID NO: 8)<br>Leu-Pro-Met-Phe-Ser-Pro (SEQ ID NO: 9)<br>Ac-Pro-Leu-Ala-Ser~Nva-Trp-NH$_2$ (SEQ ID NO: 10)<br>$^{183}$R-W-T-N-N-F-R-E-Y$^{191}$ (SEQ ID NO: 11)<br>Pro-Glo-Gly~Ile-Ala-Gly (SEQ ID NO: 12)<br>Pro-Glu-Gly~Leu-Leu-Gly (SEQ ID NO: 13) | 6.47 |
| | | MMP-8 | Collagenase -2, neutrophil Collagenase | 75 | 58 | Collagens (I, II, III, V, VII, VIII, and X); gelatin; entactin; aggrecan; tenascin, fibronectin, ProMMP-1,2 | GPQG~IWGQ (SEQ ID NO: 14)<br>Pro-Leu-Glu/Ala~Tyr-Trp-Ser (SEQ ID NO: 15 and SEQ ID NO: 16)<br>2,4-DNP-Pro-Gln-Gly-Ile-Ala-Gly-D-Arg-OH (SEQ ID NO: 17) | 6.38 |
| | | MMP-13 | Collagenases -3, rat interstitial Collagenase | 52 | 42 | Collagens (I, II, III, IV, IX, X, XIV); gelatin; entactin; aggrecan; tenascin, plasminogen; aggrecan; perlecan; fibronectin; fibrinogen/fibrin; osteonectin; MMP-9, ProMMP-9,13 | Mca-Pro-Leu-Gly-Leu-Dpa-Ala-Arg-NH$_2$ (SEQ ID NO: 18)<br>Gly-Pro-Gln-Gly~Leu-Ala-Gly-Gln779 (SEQ ID NO: 19)<br>Asp-Val-Gly-Glu-Tyr-Asn-Val-Phe88 (SEQ ID NO: 20) | 5.32 |
| MMP Families | Gelatinases | MMP-2 | Gelatinase A, 72-kDa gelatinase, Type IV collagenase | 71 | 62 | Gelatinins; fibronectin; elastin; Collagens (I, IV, V, VII, X, XI); laminin; aggrecan; vitronectin; decorin; IGFBP-3/5 | GPQG~IFGQ (SEQ ID NO: 21)<br>Mca-Pro-Leu-Gly~Leu-Trp-Ala-Arg-NH$_2$ (SEQ ID NO: 22)<br>Ac- Pro-Leu-Ala~$^s$Nva-Trp-NH$_2$ (SEQ ID NO: 23)<br>Pro-Gln-Gly~Ile-Ala-Gly-Gln (SEQ ID NO: 24) | 5.26 |

Figure 6B – Proteases involved in wound healing and their substrate specificity

| Proteases | | Enzyme Name(s) | | MW(kDa) | | Substrate | Substrate specificity | pI |
|---|---|---|---|---|---|---|---|---|
| | | MMP | Other names | latent | active | | | |
| MMP Families (cont'd) | Gelatinases (cont'd) | MMP-9 | Gelatinase B, 92-kDa gelatinase, Type V collagenase | 76 | 67 | Collagens (IV, V, VII, X, XIV, XVII); gelatin; entactin; aggrecan; elastin; fibronectin; fibrinogen/fibrin; osteonectin; plasminogen; MBP; IL-1beta | GPLG~IAGQ (SEQ ID NO: 25) Pro-Leu-Gly-Met-Leu-Ser-His (SEQ ID NO: 26) | 5.69 |
| | Stromelysins | MMP-3 | Stromelysin-1, Transin, CAP, proteoglycanase | 52 | 43 | Collagens (III, IV, V, and IX); gelatin; aggrecan; perlecan; decorin; laminin; elastin; caesin; osteonectin; ovostatin; entactin; plasminogen; MBP; IL-1beta; MMP-2/TIMP-2; MMP-7; MMP-8; MMP-9; MMP-13 | Mca-RPKPVE~ZWRK(dnp)-NH$_2$ (SEQ ID NO: 27)<br><br>Dnp-RPLA~XWRS, when X equals:<br>Leu (SEQ ID NO: 28)<br>Phe (SEQ ID NO: 29)<br>Tyr (SEQ ID NO: 30)<br>Trp (SEQ ID NO: 31) | 5.77 |
| MMP Families | Stromelysins | MMP-10 | Stromelysin-2, Transin-2 | 52 | 44 | Collagens (II-V); gelatin; caesin; aggrecan; entactin; elastin; vitronectin; fibrinogen/fibrin; laminin, MMP-1; MMP-8 | Asp-Val-Gly-His-Phe-Ser-Ser-Phe85 (SEQ ID NO: 32)<br>Gly-Pro-His-Leu-Leu-Val-Glu-Ala29 (SEQ ID NO: 33) | 5.49 |
| | | MMP-11 | Stromelysin-3, Purin motif | 51 | 46 | Laminin; fibronectin; aggrecan; IGFBP-1 | Ala-Ala-Gly-Ala-Met-Phe-Leu-Glu354 (SEQ ID NO: 34)<br>Arg-Val-Gly-Phe-Tyr-Glu-Ser-Asp688 (SEQ ID NO: 35)<br>Lys-Ala-Leu-His~Val-Thr-Asn-Ile144 (SEQ ID NO: 36)<br>Dns-Pro-Leu-Ala~Cys(OmcBzl)-Trp-Ala-Arg-NH$_2$ (SEQ ID NO: 37) | 6.25 |

Figure 6C – Proteases involved in wound healing and their substrate specificity

| Proteases | | Enzyme Name(s) | | MW(kDa) | | Substrate | Substrate specificity | pI |
|---|---|---|---|---|---|---|---|---|
| | | MMP | Other names | latent | active | | | |
| MMP Families (cont'd) | Other MMPs | MMP-12 | Macrophage metalloelastase, metalloelastase | 52 | 20 | Collagen IV; gelatin; elastin; casein; fibronectin; vitronectin; laminin; entactin; MBP; fibrinogen/fibrin, plasminogen | Leu-Val-Glu-Ala-Leu-Tyr-Leu-Val-Cys$O_3$H-Gly20 (SEQ ID NO: 38) Dnp-Arg-Pro-Leu-Ala-Leu-Trp-Arg-Ser-$NH_2$ (SEQ ID NO: 39) Arg-Pro-Phe-Glu-Val-Lys-Asp-Thr203 (SEQ ID NO: 40) Gly-Ala-Met-Phe-Leu-Glu-Ala-Ile356 (SEQ ID NO: 41) | 8.75 |
| Serine Proteases | Neutrophil elastase | - | - | 28.57806 | | Elastin | MeO-Suc-Ala-.Ala-Pro-Val-pNA (SEQ ID NO: 42) | 9.31 |
| | Thrombin | | Factor II, coagulation | | | Collagens | Benzoyl-Phe-Val-Arg-pNA,HCl | |
| | Elastase | - | - | | 25 | Elastin | | 8.0-8.5 |

PARTICLES

The present invention relates to particles. More particularly, it relates to the selective disassembly and/or assembly of particle aggregates in response to enzymes. In certain aspects, the disassembly of particle aggregates in response to enzymes is used in the diagnosis and treatment of disease.

Extensive research efforts have recently been directed toward the controlled assembly and disassembly of inorganic nanoparticles to generate novel materials and devices, potentially useful for sensing, catalysis, transport and other applications in medicinal and engineering science (Niemeyer, *Angew. Chem. Int. Ed.* 2001, 40, 4128). These tunable and/or switchable nano-materials have potential for certain applications in medical science, such as biosensing and drug delivery. For such applications, the ability dynamically to assemble and disassemble such structures as triggered by physiologically accessible environmental conditions would be valuable (Stevens, et al, *Advanced Materials*, 2004 16, 915). Previous studies have described the use of the highly specific biomolecular recognition systems of DNA, the streptavidin/biotin system and antibody/antigen systems to direct nanoparticle (dis-)assembly (Mirkin, et al, *Nature* 1996, 382, 607; Rosi & Mirkin, *Chem. Rev.*, 2005, 105, 1547-1562; Katz & Willner, Angewandte Chemie, 2004, 43, 6042-6108). These systems have tremendous potential as diagnostic tools as they are sensitive, give a fast response, don't rely on specialised equipment and are compatible with biological conditions. Stimuli that can be used to (dis-)assemble nanostructures include temperature, solvent polarity, ion concentration (including pH), light, magnetic or electric fields. These stimuli usually disrupt the micro environment and hence are not always compatible with biological fluids. Most biological interactions can only withstand fairly narrow environmental fluctuations.

A number systems have recently been described that exploit the catalytic action of enzymes to control the assembly state of nanoparticles, with applications in biosensing. In these systems, the nanoparticle surface is modified with enzyme-sensitive molecules that can form covalent or non-covalent interactions with tethered groups on neighbouring nanoparticles. When triggered by an enzyme, assembly or disassembly of nanoparticles may occur. Zhao et al used an approach involving magnetic nanoparticles as magnetic relaxation switches to detect protease activity (Zhao, et al, *Angew. Chem., Int. Ed.*, 2003, 42, 1375-1378). In this approach, protease-sensitive sequences were flanked at both termini by biotin molecules, while the nanoparticles were coated with avidin. In this approach, the enzyme action is followed by the separate addition of nanoparticles. As such, it currently does not lend itself to real-time monitoring of enzyme action. Kanaras et al. demonstrated that a number of DNA restriction and ligation enzymes can be used to assemble different populations of DNA coated gold nanoparticles (Kanaras, et al, *Angew. Chem., Int. Ed.*, 2003, 42, 191-194). In this approach, two or more separate populations of nanoparticles are required.

The present inventors have found a strategy for the reversible assembly/disassembly of nanoparticle aggregates which is triggered by enzyme reactions and hence can be applied to biological fluids.

In a first aspect, the present invention provides a particle aggregate comprising particles linked to other particles via linkers that are capable of being cleaved by an enzyme.

In a second aspect, the present invention provides a method for making a particle aggregate of the first aspect comprising: linking particles to other particles via linkers that are capable of being cleaved by an enzyme.

In one embodiment, the particles are linked directly to other particles by the linkers. In another embodiment, the particles are linked indirectly by means of a binding moiety. In this embodiment, the particles are linked to the binding moiety by the linker and the binding moieties bind to each other. In either embodiment, cleavage of the linker by the enzyme may be reversible or irreversible.

In a third aspect, the present invention provides a particle coupled to a binding moiety via a linker that can be cleaved by an enzyme.

The present invention will be described further with reference to the accompanying, non-limiting drawings, in which:

FIG. 3 illustrates two different approaches for enzymatic disassembly of particles in accordance with the present invention;

Figure 7:
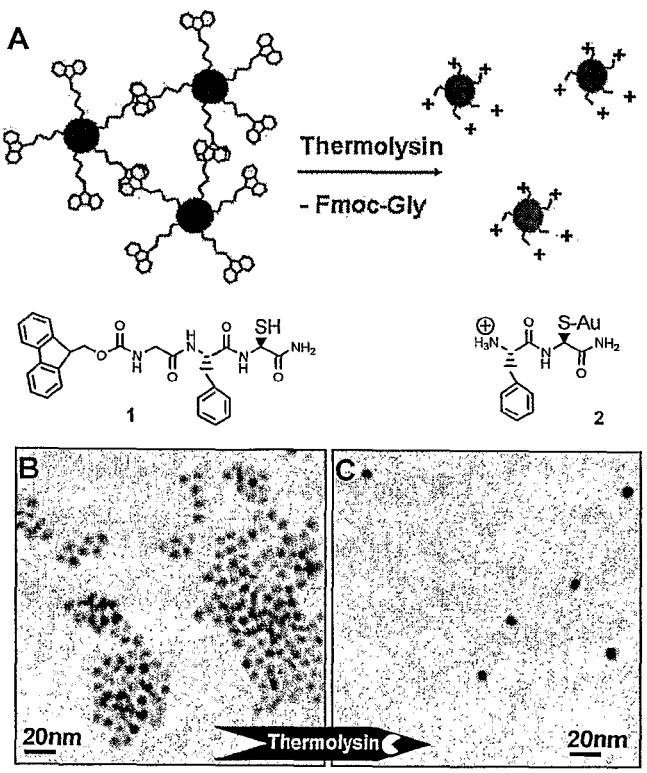
Figure 8:
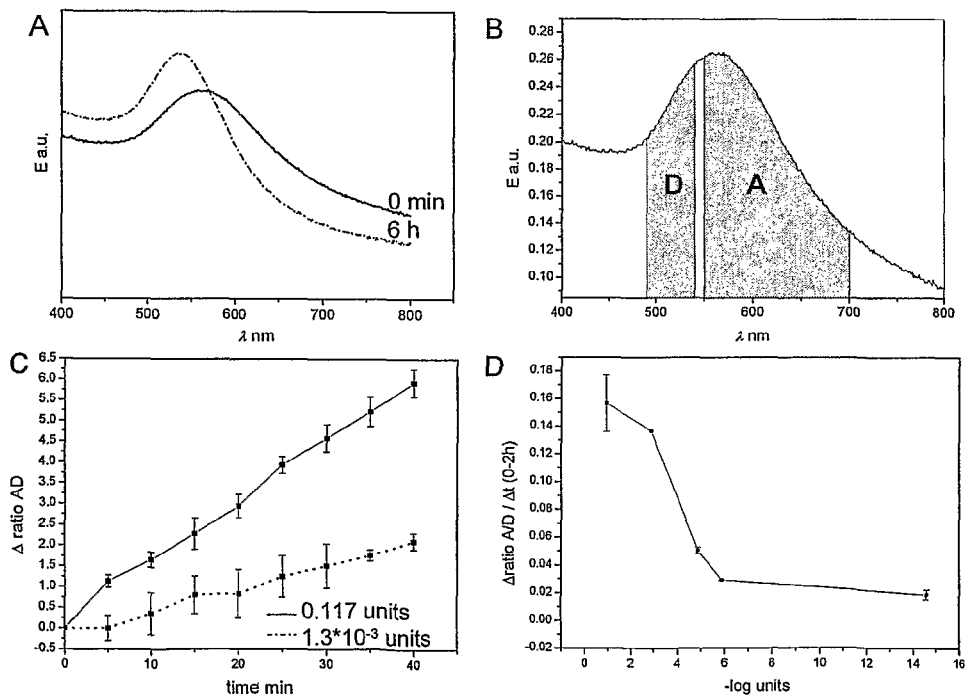
Figure 9:
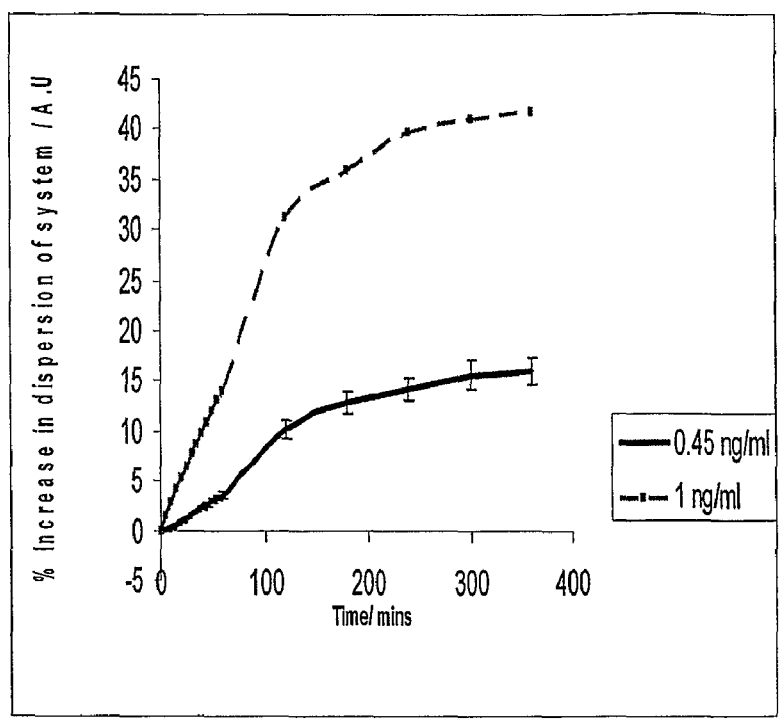

FIGS. 6A-C is a table describing proteases involved in wound healing;

FIG. 7A illustrates one particle aggregate in accordance with the present invention and how it can be disassembled by a protease, thermolysin; FIG. 7B is a transmission electron microscope (TEM) image of 8.5 nm of gold nanoparticles at pH 8 after functionalisation with peptide 1 as described in the Example herein; and FIG. 7C is a corresponding TEM image following addition of thermolysin;

FIG. 8A shows UV-visible spectra of Fmoc-Gly-Phe-Cys-$NH_2$ gold (solid line) prior to addition of enzyme and $^+$Phe-Cys-$NH_2$-gold at 6 h (dotted dashed line) following addition of 7.2 nM thermolysin; FIG. 8B is a plot of UV-visible spectra showing the areas of the curve that were computed for all samples; FIG. 8C is a graph plotting Δ ratio A/D at 5 min intervals for 7.2 nM and 1 nM concentrations of thermolysin; and FIG. 8D is a graph plotting {(Δ ratio A/D)/Δt} at 2 h versus −log [thermolysin]; and FIG. 9 is a graph plotting the percentage change in intensity against time when 0.45 ng/ml (solid line) and 1 ng/ml (dotted line) PSA is added to an aggregate of gold nanoparticles held together by a peptide capable of being cleaved by PSA.

In the present invention, enzymes are used to control the linkage between particles and hence mediate the disassembly and/or assembly of particle aggregates. Enzymes have considerable advantages over conventional chemistry methods in this regard:

they are uniquely chemo-, regio- and enantioselective;
they work under mild conditions (e.g. aqueous, pH 5-8);
many catalyse reactions near surfaces in vivo and are therefore well-equipped to catalyse reactions at interfaces (Castner & Ratner, *Surface Science* 2002. 500, 28);
their reactions are reversible under appropriate conditions and the favoured direction can be tuned at surfaces (indeed, it has recently been demonstrated that both lipases and proteases can be used for "hydrolysis in reverse", i.e. coupling of amines or alcohols to carboxylic acids at surfaces under appropriate conditions (Doezé, et al, *Chem., Int. Ed. Eng.* 2004 43, 3138; Ulijn, et al, *J. Am. Chem. Soc.* 2002 124, 10988; Humphrey, et al, *J. Am. Chem. Soc.* 2002 125, 13952; Ulijn, et al, *Org. Biomol. Chem.* 2003 1, 1277);

with modern molecular biology techniques, a wide spectrum of enzymes with different selectivities is readily available;

they play key roles in essential cellular processes and in disease states and materials that respond to these enzymes are therefore of interest to diagnostics and enzyme-responsive drug delivery.

It has been demonstrated that enzymes can be active near surfaces where non-fouling linkers such as polyethylene glycol (PEG) are incorporated (Doezé, et al, *Chem., Int. Ed. Eng.* 2004 43, 3138; Ulijn, et al, *J. Am. Chem. Soc.* 2002 124, 10988; Bosma, et al. *Chem. Commun.,* 2003 2790-2791; Humphrey, et al, *J. Am. Chem. Soc.* 2002 125, 13952; Ulijn, et al, *Org. Biomol. Chem.* 2003 1, 1277; Ulijn, et al *J. Chem. Soc., Perkin Trans.* 2 2002, 1024; Mrksich, *Curr. Opin. Chem. Biol.* 2002, 6, 794; Tirrell, et al, *Surface Science* 2002, 500, 61). When nanoparticles are used, the requirement for non-fouling linkers may be less due to a decrease in nonspecific protein adsorption with increased surface curvature (Vertegel, et al, *Langmuir,* 2004, 20, 6800-6807). It has also been demonstrated that enzymes can interact with surface tethered functional groups on nanoparticles without loss of activity or folded structure (Shenar & Rotello, *Acc. Chem. Res.* 2003, 36, 549).

The linkers may be covalently linked to the particle. Alternatively, they may be attached to the linker by means of non-covalent interactions, such as ionic bonds, hydrophobic interactions, hydrogen bonds, Van der Waals forces, dipole-dipole bonds, and pi-pi interactions.

Linkers suitable for use in the present invention are those that are capable of being cleaved, specifically or non-specifically, by an enzyme, such as a hydrolase. Hydrolases have the ability to cleave (or couple) a variety of molecules to appropriate surfaces with high selectivity, allowing the disassembly and/or assembly of nanoparticle aggregates to be selectively controlled. In one embodiment, the linker is a peptide, which can be cleaved by a protease. An estimated 2-3% of the mammalian proteome consists of proteases: enzymes that hydrolyse proteins and peptides (Rawlings, et al, *Nucleic Acids Res.* 2002, 30, 343). Many of these enzymes are involved in essential physiological functions such as immunological defence and cell differentiation. Several proteases are involved in disease states, such as HIV, Alzheimer's disease, Hepatitis C, *Candida* infections and pancreatitis (Maly, et al, *ChemBioChem* 2002, 3, 16; Davis, et al, *Proc. Natl. Acad. Sci. U.S.A.* 2002, 99, 2222-2227). Materials that are triggered by these enzymes allow for their accurate detection and quantification directly in biological fluids and also can allow localised drug delivery at the site were the drug is required.

Suitable peptide linkers may comprise 2, 3, 4, 5, 6 or more amino acids. Linkers having about 6 amino acids may be particularly useful as many enzymes recognise 3 amino acids either side of the cleavage site.

Examples of proteases include serine proteases (such as trypsin, alpha-1 proteinase, chymotrypsin, thrombin), threonine proteases, cysteine proteases (such as papain, cathepsin B, Interleukin-1-beta Converting Enzyme (ICE)), aspartic acid proteases (such as plasmepsin and HIV-1 protease), metalloproteases (such as thermolysin), and glutamic acid proteases. Other proteases are described in FIGS. 6A-C.

The present invention is not restricted to the linker being a peptide. In other embodiments, the linker can be a sugar that can be cleaved by a glycosidase, a lipid that can be cleaved by a lipase, a nucleic acid that can be cleaved by a nucleosidase or restriction enzyme, an ester that can be cleaved by an esterase. Indeed the linker can be any moiety that can be cleaved by an enzyme that breaks a bond, including kinases, phosphatases, glycosidases, glycosyltransferases, oxidases and reductases.

In the present invention, cleavage of the linker by the enzyme may result in a repulsion moiety being revealed on the particles (whether directly on the particle or on the part of the linker remaining on the particle after cleavage) which enhances disassembly of the aggregate because of repulsion between the repulsion moieties. The repulsion moiety may be a charged (negative or positive) moiety which repels other such moieties by electrostatic repulsion. Where the linker is a peptide, the charged moiety may be positively charged, and may be an amine, with cleavage of the linker creating cationic particles which repel one another. The effect can be enhanced by providing zwitterionic peptide linkers with oppositely-charged amino acids on either side of the scissile bond. Other means of inducing dispersion could include removal of attractive interactions such as pi-pi interactions (through use of aromatic amino acids or other aromatic molecules). Removal of hydrophobic or hydrogen bonding groups may also be used to achieve repulsion.

Any suitable particles can be used in the invention. Examples of such particles are microparticles, i.e. particles whose size is measured in micrometres. Preferred particles are nanoparticles, i.e. particles whose size is measured in nanometers, including nanotubes and nanorods (where the width thereof is in the nanometer range). Nanoparticles may have a size of less than 50 nm and the size may be in the range of from 10 nm to 100 nm. One example of nanoparticles suitable for use in the present invention is gold nanoparticles.

As mentioned above, in one embodiment, the particles are linked indirectly by means of a binding moiety. In this embodiment, the particles are linked to the binding moiety by the linker and the binding moieties bind to each other. Any self-assembling motif (e.g. receptor-ligand or protein motif) may be used as a binding moiety. Suitable binding moieties are preferably polyvalent. The binding moieties may bind to one another by means of non-covalent or covalent interactions. In one embodiment, the binding moieties bind to one another by virtue of their hydrophobicity, i.e. the hydrophobic binding moiety assures that the aggregate forms in aqueous media. Examples of suitable hydrophobic binding moieties include any aromatic compound, i.e. any compound that comprises at least one benzene ring. The person skilled in the art will appreciate that there are many different types of aromatic compounds available that could be attached to the linker, and which would interact with each other to form particle aggregates. However, examples of suitable hydrophobic binding moieties to which the linker may be attached include benzoyl (Bz) or carboxybenzoyl (Cbz), both of which are common protecting groups used in peptide synthesis. One example of a hydrophobic binding moiety is Fmoc, Fluorenyl methoxy carbonyl. Further examples may include naphthalene, phenylalanine thiophene, tyrosine, tryptophan, dansyl, pyrene and pyridine. In other embodiments, the binding moieties bind to one another by virtue of their hydrophilicity, through ionic bonds, hydrogen bonds, Van der Waals forces, and dipole-dipole bonds or through electrostatic interactions or biomolecular recognition.

Figure 1:
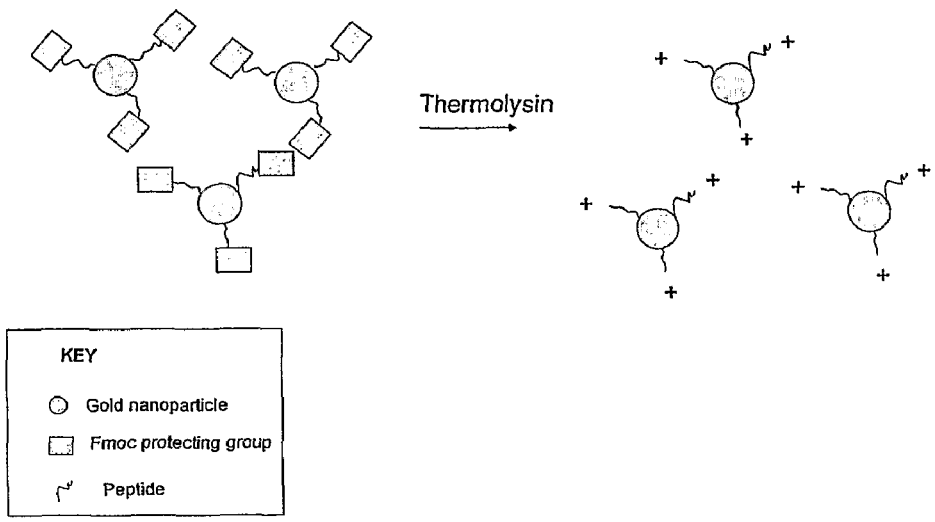
FIG. 1 illustrates one particle aggregate in accordance with the present invention and how it can be disassembled by a protease, thermolysin.
Figure 2:
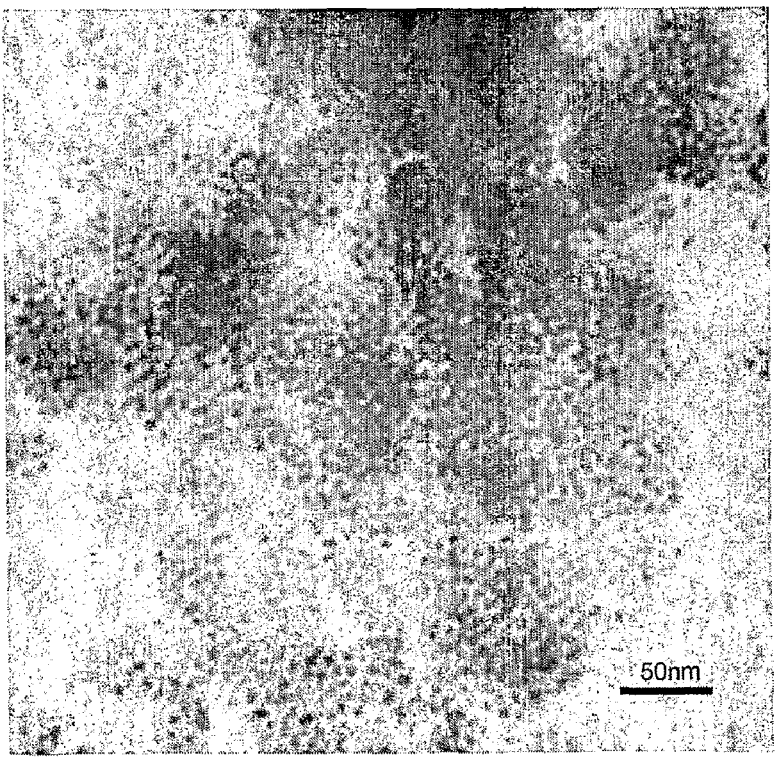
FIG. 2a is a transmission electron microscope image of an assembled nanoparticle aggregate in accordance with the present invention.
FIG. 2b is a transmission electron microscope image of the nanoparticle aggregate after exposure to an enzyme.

FIG. 1 illustrates how one particle aggregate in accordance with the present invention can be disassembled by a protease, thermolysin. A particle (in this case, a gold nanoparticle) is coupled to a binding moiety (in this case, an Fmoc group) by means of a linker (in this case, a peptide). The hydrophobicity of the Fmoc groups in aqueous solution causes them to attract each other, forming a particle aggregate. However, when the aggregate is exposed to an enzyme (in this case the protease, thermolysin), the linkers are broken and the particle aggregate is dispersed. This dispersion can be measured spectrophotometrically using UV Visible spectroscopy or transmission electron microscopy (TEM) (FIG. 2).

FIG. 3 (Approach 1) illustrates one particle aggregate in accordance with the present invention. In this, a single population of particles is modified with cysteine-containing peptides having a protease-cleavable linker and an Fmoc group. Upon enzymatic cleavage of the peptide linker, the hydrophobic group is removed and a positive charge is revealed (amine), thus triggering disassembly through electrostatic repulsion between cationic particles.

In another embodiment, the particles are linked directly to other particles by the linkers. FIG. 3 (Approach 2) illustrates one particle aggregate in accordance with this embodiment of the present invention. Two different populations of peptide-modified particles, each modified with cysteine-containing peptides, are used and are assembled to the particles either via the C- or N-terminus. These modified particles form building blocks for a reversible system. A suitable protease that is able to recognise the peptide sequences will reversibly assemble or disassemble these particles via a reversible hydrolysis reaction. The equilibrium position between peptide material and individual particles will depend on factors such as the ionic strength and pH of the medium, and on the presence of organic co-solvents and may be tunable.

Figure 4:
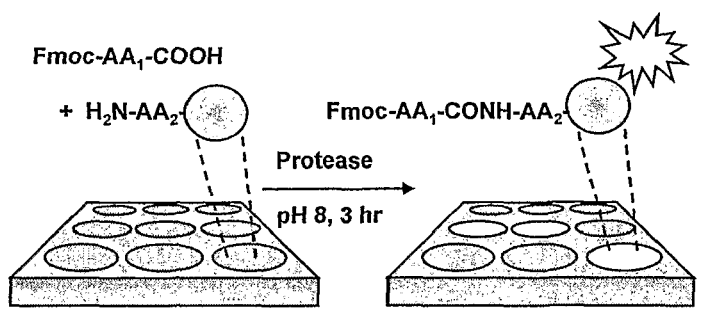
FIG. 4 illustrates how assembly and dis-assembly of particle aggregates in accordance with the present invention can be used to screen for the specificity of enzymes.

While hydrolysis of amide bonds in peptides is observed in dilute aqueous solutions, the reversal, i.e. amino acid coupling to synthesise peptides has been demonstrated at the solid/liquid interface. This discovery allows for the efficient peptide synthesis directly on solid phase catalysed by a protease that could be applied in protease specificity screening. FIG. 4 illustrates how proteases can be used to couple soluble fluorescent (Fmoc) tagged amino acids ($AA_1$) to surface immobilised amino acids ($AA_2$) in a selective "reverse hydrolysis" reaction, using a micro array format to measure the amino acid preference of a protease, i.e. a fluorescent signal is observed only when the protease being screened is able for form a peptide bind between the surface immobilised amino acids ($AA_2$) and the soluble fluorescent (Fmoc) tagged amino acids ($AA_1$). Similarly, lipase catalysed hydrolysis of esters could be reversed to synthesize esters on solid support. These observations indicate that hydrolases can be employed both for hydrolysis and coupling reactions when the ligands are tethered to a solid surface.

For the avoidance of doubt, it will be appreciated by those skilled in the art that the particle aggregates illustrated in FIGS. 2, 3 and 4 can have linkers other than the peptide linkers illustrated, as is described above.

The present invention can be used in the diagnosis and treatment of diseases. The disassembly of a particle aggregate can indicate the presence of a particular enzyme and hence be diagnostic of a disease or condition. Thus, in further aspects, the present invention provides a particle aggregate of the first aspect or a particle of the third aspect for use in medicine. The present invention also provides the use of a particle aggregate of the first aspect or a particle of the third aspect in the manufacture of a diagnostic for diagnosing a disease or condition associated with the enzyme. For example, prostate cancer can be diagnosed by detecting Prostate Specific Antigen (PSA) using the present invention. Using particles including a linker that is specifically cleaved by PSA (such as SSFYSGGGC (SEQ ID NO: 1) for example), PSA can be detected by monitoring dispersion of an aggregate in accordance with the invention.

Disassembly of the particle aggregate can be monitored by a colour change in solution. It may also be monitored by spotting the solution on a TLC plate to see a red or blue dot (rapid throughput screening or could be accessible to simple in vitro diagnostic kit for us in hospital or GP clinic).

In addition, the disassembly of a particle aggregates in accordance with the present invention by an enzyme can be used for drug delivery. Thus, a drug can be retained within a particle aggregate of the invention and only be released when the particle aggregate comes into contact with an enzyme at a disease site and the aggregate is caused to disassemble by the enzyme. Therefore, in a further aspect, the present invention provides:

a particle aggregate which comprises particles linked to other particles via linkers that are capable of being cleaved by an enzyme and a drug, wherein the drug is retained in the aggregate until the linkers are cleaved by the enzyme;

a method for the treatment of a disease or condition associated with an enzyme, comprising: administering to a patient suffering from the disease or condition a particle aggregate which comprises particles linked to other particles via linkers that are capable of being cleaved by an enzyme and a drug, wherein the drug is retained in the aggregate until the linkers are cleaved by the enzyme; and the use of a particle aggregate which comprises particles linked to other particles via linkers that are capable of being cleaved by an enzyme and a drug, wherein the drug is retained in the aggregate until the linkers are cleaved by the enzyme in the manufacture of a medicament for the treatment of a disease or condition associated with the enzyme.

As mentioned above, it is known that several proteases are involved in disease states, including HIV, Alzheimer's Disease, Hepatitis C, *Candida* infections, pancreatitis, cancer, inflammation and wound healing.

Medicaments in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carriers) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions oils (e.g. vegetable oils) may be used to provide oil-in-water or water in oil suspensions. Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6):318 (1986). Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas. Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient. Pharmaceutical compositions adapted for administration by inhalation include fine particle dusts or mists which may be generated by means of various types of metered dose pressurised aerosols, nebulizers or insufflators. Pharmaceutical compositions adapted for vaginal administration may be presented as pessaries, tampons, creams, gels, pastes, foams or spray formulations. Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substances of the present invention can vary between wide limits, depending upon the disease or disorder to be treated, the age and condition of the individual to be treated, etc. and a physician will ultimately determine appropriate dosages to be used. The dosage may be repeated as often as appropriate. If side effects develop the amount and/or frequency of the dosage can be reduced, in accordance with normal clinical practice.

The particle aggregates of the present invention may be used for testing for the presence of enzymes in aqueous samples. If an enzyme being detected is specific for a particular microorganism, such as *E. coli*, the test will indicate the presence of that microorganism. Thus, an array of particle-linker-'binder' linkages that are specific to certain microorganism-related enzymes could indirectly test for many different microorganisms in parallel. One example where such an assay could be used is in testing for drinking water quality. For example, β-D-glucoronidase may be indicative of the presence of *E. coli*; β-D-galactosidase and β-D-glucosidase can be used to detect coliform and enterococci resp., which are indicators of microbiological activity in water (see Manafi, OECD Worksop Molecular Methods for Safe Drinking Water, Interlaken '98, 1-16).

More specific, but non-limiting, ways in which the invention can be carried out and used will now be described. Where the present invention involves peptide linkers, these peptides can be immobilised on the surface of gold nanoparticles as follows. Different populations of gold nanoparticles (NP) ranging from 10 nm to 50 nm but not limited to this size-range are used. The particles are first stabilised for example by complexation with di-potassium bis(p-sulfonatophenyl)phenylphosphine dihydrate. Peptides with terminal cysteine residues (either at N- or C-terminus of the peptide chain) are synthesised and added to solutions of gold nanoparticles (TedPella, Redding, Calif.) to allow the sulphur groups of the cysteine residues to bind directly to the gold surface. The peptide/nanoparticle coupling efficiency is monitored by separating the NPs from solution by gentle centrifugation, the decrease in soluble peptide concentration is then followed by high performance liquid chromatography (HPLC) and UV Visible spectroscopy. In addition, InfraRed (IR) spectroscopy is employed to measure and quantify the presence of amides on the surface, as recently demonstrated in Shenar & Rotello, *Acc. Chem. Res.* 2003, 36, 549. Peptides are synthesised either manually or using an automated peptide synthesiser using Fmoc strategies that are well-known in the art.

For approach 1 set out in FIG. 3, Fmoc-Phe-Phe-Gly-Cys-NP (SEQ ID NO: 2) is synthesised, as these modified peptides will be cleaved by thermolysin from *B. thermoproteolyticus* Rokko. For approach 2 set out in FIG. 3, both NP-Cys-Gly-Gly and Phe-Gly-Cys-NP are prepared as a substrate for thermolysin. Thermolysin is a very stable enzyme that prefers to hydrolyse (or synthesise depending on the equilibrium of its reaction) peptide bonds at the N-terminus of hydrophobic amino acids and is rather non-specific for the C-terminal amino acids. Gold nanoparticles that carry C- and N-terminally immobilised amino acids are first coupled chemically to produce the assembled starting material. Chemical coupling of the nanoparticles is carried out in dimethyl formamide (DMF) using conventional hydroxybenzotriazole/diisopropyl carbodiimide coupling agents. A 1:1 mixture of NP-Cys-Gly-Gly and Phe-Gly-Cys-NP is used initially. The efficiency of chemical coupling is assessed using transmission electron microscopy (TEM) and IR spectroscopy. Chemically-assembled nanoparticle structures are isolated from the reaction medium by gentle centrifugation and resuspension in buffered solution.

To test whether proteolytic enzymes can cleave peptides that are linked to nanoparticles, Fmoc-terminated oligopeptides are immobilised onto NPs as described above following approach 1. The peptides consist of sequences that are known to be cleaved by thermolysin (e.g. Fmoc-Phe-Phe-Gly-Cys-thermolysin (SEQ ID NO: 2) is expected to cleave between the Phe residues). The modified NPs are exposed to thermolysin for varying amounts of time, the NP suspensions are then centrifuged and the supernatant is analysed by HPLC for the presence of cleaved Fmoc-Phe. Controls involve D-peptides that should not be cleaved enzymatically (Ulijn, et al, *J. Am. Chem. Soc.* 2002 124, 10988).

Glycine linkers of different lengths can be used to assess the optimum linker length. Polyglycine gives optimal conformational flexibility and can be coupled straightforwardly using solid phase synthesis. Fmoc-Phe-Phe-(Gly)$_n$-Cys with n=3 (SEQ ID NO: 3), 5 (SEQ ID NO: 4), 10 (SEQ ID NO: 5) glycine residues can be compared. As a control experiment, nanoparticles modified with Fmoc-(D)Phe-Phe-(Gly)$_n$-Cys are used. Here, no enzymatic hydrolysis and hence no nanoparticle dis-assembly should be observed since thermolysin exclusively recognises L amino acids. TEM of the initial and final nanoparticle assemblies is performed.

Taking approach 1 described above, enzyme concentrations can be quantified using a colorimetric assay. To individual wells of a 96 well plate containing optimised amounts of aggregated peptide nanoparticles, different concentrations of thermolysin are added (although any enzyme being assayed could be used with an appropriate linker) and the kinetic response measured in real time using a colorimetric plate reader by taking advantage of the shift that occurs in the surface plasmon resonance peak in the UV-visible spectra.

Taking approach 2 described above, conditions (enzyme concentration, pH, ionic strength) are chosen to allow the aggregation of nanoparticles to be followed in real time using UV-Visible spectroscopy. As the nanoparticles aggregate and form larger assemblies, this will be reflected in a red shift in the surface plasmon resonance peak in the UV-visible spectra. Different concentrations of enzyme are used in individual wells of a 96 well plate. Reaction rates of assembly (starting from nanoparticles) and dis-assembly (starting from assemblies) are compared. Due to the carboxylic acid and amine particles formed in these reactions, non-specific aggregation through electrostatic attraction may be observed. The main method of distinguishing between covalent (enzymatic) and noncovalent (e.g. electrostatic) aggregation is through choice of appropriate controls. Enzymatic coupling is only expected when L-amino acids are used, hence any aggregation observed when using D-amino acids will be non-covalent. Another method is to add cosolvents to disrupt any non-covalent interactions: non-covalent assemblies will disassemble whilst covalent assemblies will stay intact. Variation of ionic strength by using common salts (KCl, NaCl) or high ionic strength buffers are used to identify conditions where non-specific aggregation is minimised.

Various factors affect the equilibrium position of the enzymatic NP assembly reaction. The overall equilibrium constant can be expressed as the ratio of assembled particles over free particles ($K_{eq}=NP_{ass}/(NP_1 \cdot NP_2)$). $K_{eq}$ is composed of three separate equilibria: the ionisation of the peptide NP with free carboxylic acid group ($K_1$); that of the peptide NP with free amine ($K_2$) and the amide synthesis/hydrolysis itself ($K_3$)—see FIG. 5. The amide hydrolysis equilibrium has been studied in depth previously, both in dilute aqueous media (Ulijn, et al *J. Chem. Soc., Perkin Trans.* 2 2002, 1024) and on polymer hydrogels (Ulijn, et al, *Org. Biomol. Chem.* 2003 1, 1277). Based on these previous findings, it is expected that ionisation equilibria $K_1$ and $K_2$ (FIG. 5) will contribute significantly to the equilibrium position. It is anticipated that ionisation will be suppressed when the peptides are immobilised onto NPs due to the difficulty of forming of charges in the vicinity of equal charges (i.e. many similar charges on a surface is unfavoured). $K_1$ and $K_2$ are quantified by acid-base titration of the NPs while $K_3$ is obtained from measurement of ratios of assembled and free nanoparticles using TEM, UV visible spectroscopy and IR. To assure equilibrium has been reached, the reactions will be started from both directions (i.e. free nanoparticles and assembled structures prepared as described above).

The ionic strength of the solution is expected to contribute significantly towards the equilibrium position of the peptide hydrolysis/synthesis. Ionisation is expected to be significantly suppressed in low ionic strength media, leading to increased synthesis and resultant NP assembly. At high ionic strength hydrolysis, disassembly is expected to be favoured. These effects can be quantified by titrating both NP's with free acid and amine termini at different ionic strength values (obtained using buffered solutions at different concentrations). The dependence of the overall equilibrium constant $K_{eq}$ on ionic strength is quantified using the methods described above.

Conditions are selected where the balance between entropy and enthalpy allows for assembly under near equilibrium conditions. This allows reversible assembly and a degree of error corrections thus ensuring that the most stable structures are formed.

Figure 5:
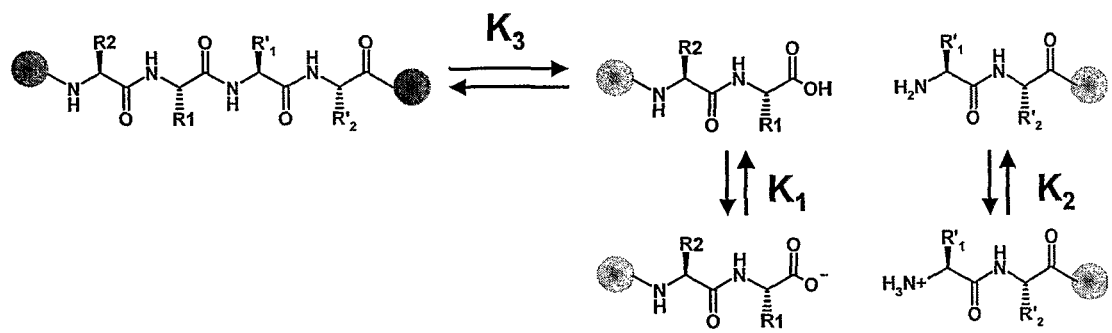
FIG. 5 illustrates the equilibrium constants of reversible particle assembly in accordance with the invention.

The primary specificity of peptide hydrolysing enzymes describes the preference for the amino acids on either side of the amide bond (amino acids with side chains R1 and R'1—see FIG. 5). To test the validity of this approach, three different proteases are compared: commercially-available bovine pancreatic α-chymotrypsin, thermolysin from *B. thermoproteolyticus* Rokko, and elastase from hog pancreas. These proteases display opposite but complementary specificities for certain R1/R'1 amino acid combinations—see Table 1. While α-chymotrypsin is selective for hydrophobic amino acids in R1 position, it is rather unspecific for the R'1 residue. By contrast, thermolysin exhibits a preference for large hydrophobic residues in the R'1 position and is non-specific in R1. Elastase has a preference for small amino acids in both positions. Hence, it is expected that hydrolysis/synthesis of the amide bond in Gly-Leu will be catalysed by thermolysin, and that of Leu-Gly preferentially by α-chymotrypsin, etc. This highly specific behaviour has recently been demonstrated on peptides linked to polymer hydrogels (Doezé, et al, *Chem., Int. Ed. Eng.* 2004 43, 3138). To test whether this specificity can be exploited in the specific assembly of nanoparticle mixtures, four different types of nanoparticles are prepared: N-terminal glycine-NP, C-terminal glycine-NP, N-terminal leucine-NP and C-terminal leucine-NP. Different-sized particles are used to allow for easy distinction between them. Whether all three enzymes are catalytically active on NP immobilised peptides is assessed. The conditions are optimised and the quaternary mixtures of NPs are exposed to each of the enzymes named above. Whether aggregation of nanoparticles is only observed for the combination of nanoparticles that agrees with the enzymes selectivity is assessed. The assembly process is monitored by UV-Visible spectroscopy and TEM. Enzyme amounts are reduced as far as possible to establish the sensitivity of the system. These experiments provide proof of concept of the use of these materials in biosensing.

TABLE 1

Specificity of four different model proteases that are used to assess the selectivity of nanoparticle assembly.

| Enzyme | Gly-Gly | Gly-Leu | Leu-Leu | Leu-Gly |
|---|---|---|---|---|
| α-chymotrypsin (EC 3.4.21.1) | No | No | yes | Yes |
| elastase (EC 3.4.21.36) | Yes | No | no | No |
| thermolysin (EC.3.4.24.27) | No | Yes | yes | No |

Amino acids are linked to nanoparticles via cysteine residues. Yes/No indicates whether NP assembly is expected or not.

As a specific example of a biomedically-relevant application of the nanoparticle assemblies of the invention, matrix metalloproteases (MMPs) in chronic wound fluids are studied. There is an urgent need for devices that allow for the accurate and direct measurement of protease activity within fluids of non-healing (chronic) wounds, which currently requires dilution and pH adjustment of the fluid (Greener, B., et al, *J. Wound Care*, 12, 2). These MMPs are capable of selectively hydrolysing specific peptide sequences consisting of at least 6 amino acid residues for optimal cleavage. MMPs that play key roles in wound healing are identified, and a nanoparticle/peptide system is designed and tested for selectivity (detection of single MMP in biological fluids), sensitivity (what is the minimum concentration that can be detected) and reproducibility using 96 well plate format.

FIGS. 6A-C provide details of:—(i) collagenases (MMP-1, MMP-8, MMP-13); (ii) gelatinases (MMP-2, MMP-9); (iii) stromelysin (MMP-3, MMP-10, MMP-11); and (iv) MMP-12. In addition, FIGS. 6A-C give details of neutrophil elastase, thrombin and elastase. FIGS. 6A-C also provide details of the various substrates for each protease listed, and in addition, give detail about the substrate specificity of each protease of interest (target protease), i.e. the sequence of amino acids, which each protease recognises and can hydrolyse. For example, MMP-1 protease has catalytic specificity for a range of different collagens such as (I, II, III, VII, VIII, X, XI); gelatin; aggrecan; tenascin; L-selectin: IL-1Beta; proteoglycans; entactin; ovostatin; MMP-2; MMP-9. More specifically, MMP-1 recognises, and hydrolyses the following sequences:—

```
                                        (SEQ ID NO: 6)
(i)   Ac-Pro-Leu-Gly-Ser~Leu-Leu-Gly-OEt;

(SEQ ID NO: 7)
(ii)  Mca-Pro-Leu-Gly~Leu-Dpa-Ala-Arg-NH2;

(SEQ ID NO: 8)
(iii) Pro-Met-Ala~Leu-Trp-Ala-Thr;

(SEQ ID NO: 9)
(iv)  Leu-Pro-Met~Phe-Ser-Pro;

(SEQ ID NO: 10)
(v)   Ac-Pro-Leu-Ala-Ser~Nva-Trp-NH2;

(SEQ ID NO: 11)
(vi)  Arg-Trp-Thr-Asn-Asn-Phe-Arg-Glu-Tyr;

(SEQ ID NO: 12)
(vii) Pro-Glu-Gly~Ile-Ala-Gly;

(SEQ ID NO: 13)
(viii) Pro-Glu-Gly~Leu-Leu-Gly.
```

Preferred features of each aspect of the invention are as for each of the other aspects mutatis mutandis. The prior art documents mentioned herein are incorporated to the fullest extent permitted by law.

The present invention will now be described further with reference to the following non-limiting examples.

EXAMPLE 1

A Self-Assembled Peptide-Functionalised Nanoparticle Network Capable of being Actuated by Thermolysin from *B. Thermoproteolyticus* Rokko General Procedures: Gold nanoparticles with a diameter of 10 nm were purchased from BBI International (Agar Scientific, UK). Their diameter as measured by TEM (average of 100 particles) was found to be 8.5±1.0 nm. Dipotassium bis(p-sulphonatophenyl)phenylphosphine dihydrate was purchased from Strem Chemicals (MA). Unless otherwise indicated, other reagents and materials were obtained from Sigma-Aldrich (UK). All solutions were prepared using high-purity deionised water (purified on Nanopure Diamond system from Triple Red Laboratory Technology, UK).

Peptide synthesis: Amino acids and resin were purchased from Novabiochem (UK) and all other reagents for solid phase synthesis were obtained from AGTC Bioproducts (UK). Peptide 1 (Fmoc-Gly-Phe-Cys) and peptide 2 (Fmoc-Gly-d-Phe-d-Cys) were synthesised using standard solid phase Fmoc strategy. Peptides were dried in vacuum and purified by reversed-phase HPLC (Gilson) using a 20%-65% water/acetonitrile gradient containing of 0.1% TFA. The identity of the peptides was confirmed by Mass spectrometry (Micromass Ltd., Altrincham, UK) and NMR (JEOL 270NMR Spectrometer).

Functionalisation of nanoparticles with peptide: 8.5 nm gold nanoparticles were stabilised by complexation with dipotassium bis(p-sulphonatophenyl)phenylphosphine dihydrate for 12 h. The stabilised gold nanoparticles were stable in aqueous solution at room temperature over a period of months. Final solutions of stabilised gold nanoparticles (concentration as received) were prepared in 10 mM sodium phosphate (pH8) and 100 mM NaCl, and incubated at room temperature overnight with 20 µL of peptide 1 (50 µM) in N,N-dimethylformamide (DMF) to yield gold-nanoparticles conjugates. Excess peptide was removed by centrifugation and removal of supernatant prior to resuspension of the nanoparticles to initial volume with phosphate buffer (pH8), 0.05% w/v Bovine Serum Albumin (BSA), and 100 mM NaCl.

Monitoring enzymatic hydrolysis: All reactions were carried out in disposable plastic cuvettes and analysis was done in situ and in duplicate. Thermolysin solutions were freshly prepared in 10 mM sodium phosphate (pH8) at the required range of concentrations. UV-visible spectra were recorded at room temperature following addition of thermolysin to peptide functionalised gold conjugates. Spectra were recorded on a Unicam UV-500 UV-Visible Spectrophotometer over the range 200-800 nm with 1 nm resolution and background correction using phosphate buffer, NaCl, and 0.05% w/v BSA in 1 cm path-length polystyrene cuvettes were used.

TEM characterization: Electron microscopy samples were prepared on a 300 mesh holey carbon-coated copper TEM grid from Agar Scientific. A TEM grid was placed on a piece of medical tissue paper and one drop of solution was applied to the grid from a pipette. The tissue paper served to wick away excess solution. The grid was then washed with 5 drops of deionised water following the above procedure to remove excess salt from the grid surface. TEM was performed on a JEOL TEM FX(II) operated at 200 KV.

A self-assembled peptide-functionalised nanoparticle network to be actuated by thermolysin from *B. Thermoproteolyticus* rokko using the tri-peptide Fmoc-Gly-Phe-Cys-NH$_2$ (peptide 1) was designed. The terminal Cys-NH$_2$ allows facile attachment to the surface of gold nanoparticles via the formation of a gold-thiolate bond. Thermolysin exhibits a preference for large hydrophobic residues in the P1' (Phe) position, and is non-specific for the P1 (Gly) residue. Hence, it would be expected that hydrolysis of the amide bond of Gly-Phe would specifically be catalysed by thermolysin and simultaneously result in the dispersion of the nanoparticles and a visible colour change.

Transmission electron microscopy (TEM) images of stabilised gold nanoparticles revealed a well-dispersed population of nanoparticles (FIG. 7A). After functionalising with peptide 1, aggregation of the nanoparticles was observed (FIG. 7B). This observation concurs with the UV-visible surface plasmon resonance peaks where stabilised gold nanoparticles with a single peak at 522 nm (characteristic of dispersed particles), exhibited a broadening and red shift in the peak up to 565 nm upon functionalisation with peptide 1, indicating an increase in the size of nanoparticle assembly.

To test the enzyme responsiveness of the system, the peptide-functionalised nanoparticles were incubated at room temperature with concentrations of thermolysin ranging from 7.2 nM (7.2.10$^{-9}$ M) to 2.08 zM (single molecule, 2.08 10$^{-21}$ M). Transmission electron microscopy (TEM) images following addition of thermolysin reveal a well-dispersed population of nanoparticles (FIG. 7C). The UV-visible spectra shows a clear shift in the plasmon resonance peak from 565 nm to 532 nm 6 h after addition of 7.2 nM thermolysin (FIG. 8A). Similar UV-visible spectral shifts of around 30 nm were observed over different timescales for the range of thermolysin concentrations tested. HPLC of the supernatant detected the presence of Fmoc-Gly only, indicating that this was the cleaved fragment of the tripeptide 1 and thus confirming the site of enzymatic hydrolysis. In control experiments, 8.5 nm gold particles functionalised with Fmoc-Gly-Phe-Cys-NH$_2$ did not disassemble upon introduction of trypsin, an enzyme that exclusively cleaves peptides with Arg or Lys residues in the P1 position. As expected, nanoparticles functionalised with Fmoc-Gly-d-Phe-d-Cys did not disperse upon introduction of thermolysin.

Monitoring of the hydrolysis reaction by direct observation of the plasmon resonance shift is only possible for large spectral shifts. A highly sensitive and accurate method to quantify change in spectral shape can be achieved by calculation the change in the ratio A/D (Aggregated/Dispersed area) for the area under the plasmon resonance peak. FIG. 8B shows the region under which the integral was computed for the UV-visible spectra of all samples tested, with region D (dispersion) spanning from 490 to 540 nm and region A (aggregation) from 550 to 700 nm. Samples were analysed obtaining a ratio A/D for different time points. Using this approach, nanoparticle dispersion could be followed in real time (FIG. 8C). By varying the enzyme concentration, a linear dependance was observed over 4 orders of magnitude.

Single enzyme molecule detection was determined by measuring the Δ ratio A/D down to 2.08 zM thermolysin. The Δ ratio A/D increases over a period of 47 h for 7.2 nM and 2.08 zM, to 96.5% and 25.2% respectively.

FIG. 8D is the graphical representation of {(Δ ratio A/D)/Δt} for the different concentrations of thermolysin tested. For concentrations ranging from 7.2 nM down to 0.1 fM (0.1.10-12 M) thermolysin, it is possible to get a linear regression from which the enzyme concentration can be quantified.

This example illustrates an enzyme-responsive peptide-functionalised gold nanoparticle assembly system that enables rapid enzyme detection and with a much higher sensitivity (single molecule) than previously reported. The system here also offers dynamic control over the generated assemblies under mild conditions, which can prove useful for the development of a new class of biologically-controlled dynamic materials with applications in drug delivery and in in vivo monitoring of enzymes. Further, the modular approach (anchor (e.g. cystein-NH$_2$ group), enzyme cleavable linker, actuator (e.g. Fmoc)) can be used as a basis to tailor the system to easily detect a wide range of enzymes with high sensitivity.

EXAMPLE 2

Screening for Prostate Specific Antigen

Prostate cancer is currently the most prevalent form of cancer in the West and the second leading cause of cancer-related mortality in men (Mazhar, et al., BJU *International*, 2006. 98(4): p. 725-730). The method most widely used for screening and early detection of prostate cancer is the prostate specific antigen (PSA) blood test which measures the level of PSA in serum. The U.S Food and Drug Administration has approved the use of PSA test along with a digital rectal examination to help detect prostate cancer in men age 50 and older, as well as using the PSA test to monitor if prostate cancer has recurred after treatment.

The production of PSA is androgen dependent in the normal prostate gland and can be detected after puberty in the serum of healthy men. PSA is produced by the prostate gland epithelium and secreted into seminal fluid, where it can be found at concentrations of 0.2-5 g/L (Wang, et al., *Prostate*, 1981. 2(1): p. 89-96). In circulation, the concentration of PSA in healthy men is normally very low ($\leq$2.0 ng/ml) and increased levels of serum total PSA (tPSA) are associated with an increased risk of prostate cancer.

The ability to identify enzymatically-active PSA with a colorimetric sensor will help in the screening of prostate cancer, especially for men with PSA in the 2.5-4.0 ng/ml range. This example demonstrates detection of enzymatically-active PSA using the present invention.

Gold nanoparticles were functionalised with fluorenyl-9-methoxycarbonyl (Fmoc)-SSFY$\dagger$SGGGC-CONH$_2$ (SEQ ID NO: 1). The peptide sequence was chosen to be specific for PSA enzymatic cleavage (Coombs, et al., *Chem Biol*, 1998. 5(9): p. 475-88). $\dagger$ indicates the site of hydrolysis. The incorporation of a cysteine residue at the C terminus provides linkage to the gold surface via a gold-thiolate bond and aggregation of the gold nanoparticles are induced by π-π interactions between Fmoc groups at the N-terminal.

PSA at a concentration of 0.45 ng/ml or 1.0 ng/ml was added to the thus-formed aggregate and dispersion of the aggregate owing to PSA cleavage of the SSFYSGGGC (SEQ ID NO:1) peptide sequence was monitored.

FIG. 9 illustrates the experimental results obtained using this nanoparticle-based system. Discrimination of PSA concentration is seen after 5 min. The nanoparticle system is highly sensitive to low enzyme concentrations, and a distinct separation can be seen between 0.45 ng/ml and 1.0 ng/ml. Thus, the detection method selectively recognises the enzymatic form of PSA, as well as PSA-A2M (where a portion of PSA is complexed with $\alpha_2$-macroglobulin (A2M) which is not picked up by immunoassays. This is because low-molecular weight synthetic peptide substrates are used to create the gold nanoparticle-based system. The system is much simpler compared to conventional immuno-assays and provides easy detection with the visual change in colour.

The invention claimed is:

1. A nanoparticle aggregate comprising nanoparticles linked to other nanoparticles indirectly by means of a fluorenyl methoxy carbonyl (Fmoc) binding moiety, wherein the nanoparticles are linked to the Fmoc binding moiety via peptide linkers that are capable of being cleaved by a protease enzyme, wherein cleavage of the peptide linkers by the protease enzyme results in a repulsion moiety being revealed on the nanoparticles which enhances disassembly of the aggregate because of repulsion between the repulsion moieties.

2. An aggregate as claimed in claim 1, wherein cleavage of the linker by the enzyme is reversible.

3. An aggregate as claimed in claim 1, wherein cleavage of the linker by the enzyme is irreversible.

4. An aggregate as claimed in claim 1, wherein the repulsion moiety is a charged moiety which repulses other repulsion moieties by electrostatic repulsion.

5. An aggregate as claimed in claim 4, wherein the charged moiety is an amine.

6. An aggregate as claimed in claim 1, wherein the nanoparticle is a gold nanoparticle.

7. An aggregate as claimed in claim 1, further comprising a drug that is released when the peptide linkers are cleaved by the protease enzyme.

8. A method for making a nanoparticle aggregate as claimed in claim 1, comprising: linking nanoparticles to other nanoparticles indirectly by means of a fluorenyl methoxy carbonyl (Fmoc) binding moiety, wherein the nanoparticles are linked to the Fmoc binding moiety via peptide linkers that are capable of being cleaved by a protease enzyme to reveal a repulsion moiety.

9. An aggregate as claimed in claim 1, when used in a method for diagnosing a disease or condition associated with the protease enzyme, wherein a sample from a patient suspected of having the disease or condition is contacted with the aggregate, and whether the sample causes the aggregate to disaggregate is determined.

10. An aggregate as claimed in claim 1, when used in a method for the treatment of a disease or condition associated with the protease enzyme, wherein the aggregate is administered to a patient suffering from the disease or condition in combination with a drug, the drug being retained in the aggregate until the linkers are cleaved by the protease enzyme.

* * * * *